US006596515B2

(12) United States Patent
Suh

(10) Patent No.: US 6,596,515 B2
(45) Date of Patent: Jul. 22, 2003

(54) RECOMBINANT VECTOR FOR USE IN GENE THERAPY FOR INSULIN-DEPENDENT DIABETES MELLITUS AND THERAPEUTIC COMPOSITION THEREOF

(76) Inventor: Dongsang Suh, Department Genetic Engineering, Sungkyunkwan University, Chunchun-dong, Jangan-ku, Suwon, Kyonggi-do (KR), 440-746

( * ) Notice: Subject to any disclaimer, the term of this patent is extended or adjusted under 35 U.S.C. 154(b) by 0 days.

(21) Appl. No.: 09/775,508

(22) Filed: Feb. 5, 2001

(65) Prior Publication Data

US 2003/0054498 A1 Mar. 20, 2003

(30) Foreign Application Priority Data

Jan. 15, 2001 (KR) .......................................... 2001-2229

(51) Int. Cl.[7] .......................... C12N 15/66; C12N 15/85

(52) U.S. Cl. ................................. 435/91.41; 435/320.1

(58) Field of Search ............................ 435/91.41, 320.1

(56) References Cited

U.S. PATENT DOCUMENTS

2002/0001580 A1 * 1/2002 Hermonat et al.

OTHER PUBLICATIONS

Suh, D., et al., "Gene Therapy of Type 1 Diabetes Mellitus: Liposome–mediated DNA Delivery to Murine Skin", *The 55th Annual Meeting of the Korean Association of Biological Sciences*, Abstract F812, pp. 268–269, (Oct. 27–28, 2000).

* cited by examiner

*Primary Examiner*—James Ketter
(74) *Attorney, Agent, or Firm*—Nath & Associates PLLC; Gary M. Nath; Jerald L. Meyer

(57) ABSTRACT

Disclosed are a recombinant vector for use in gene therapy for insulin-dependent diabetes mellitus and a therapeutic composition thereof. Following the injection of a β-galactosidase expression vector having a K14 promoter gene, along with a Drosophola's P transposase expression helper vector, into murine skin in a liposome-mediated manner, the β-galactosidase gene is expressed in the keratinocyte layer from 24 hours to 20 weeks after injection as measured by X-gal staining. With the enhancement effect and tissue specificity, the K14 promoter is applied for the expression of a human insulin gene in keratinocytes, thereby suggesting a new gene therapy method for treating insulin-dependent diabetes mellitus. When, in combination with the P-element expression helper vector, a human insulin expression vector with the K14 promoter is injected into the skin of diabetic mice, which lack insulin-producing β-cells of the pancreas, their blood glucose levels are maintained in a normal range.

3 Claims, 10 Drawing Sheets

FIG. 7

```
K14 PROMOTER 5' ——————►
ATTGCTGAAG TTTTGATATA CACACCTCCA AAGCAGGACC AAGTGGACTC
CTAGAAATGT CCCCTGACCC TTGGGGCTTC AGGAGTCAGG GACCCTCGTG
TCCACCTCAG CCTTGCCCTT GCACAGCCCA GCTCCACTCC AGCCTCTACT
CCTCCCCAGA ACATCTCCTG GGCCAGTTCC ACAAGGGGCT CAAACGAGGG
CACCTGAGCT GCCCACACTA GGGATGTTCT GGGGGTCTGA GAAGATATCT
GGGGCTGGAA GAATAAAAGG CCCCCCTAGG CCTGTTCCTG GATGCAGCTC
CAGCCACTTT GGGGCTAAGC CTGGGCAATA ACAATGCCAA CGAGGCTTCT
TGCCATACTC GGTTTACAAA ACCCTTTACA TACATTGTCG CATTGGATTC
TCAGAGCTGA CTGCACTAAG CAGAATAGAT GGTATGACTC CCACTTTGCA
GATGAGAACA CTGAGGCTCA GAGAAGTGCG AAGCCCTGGG TCACAGAGGC
GTAAATGCAG AGCCAGGACC CACCTGAAGA CCCACCTGAC TCCAGGATGT
TTCCTGCCTC CATGAGGCCA CCTGCCCTAT GGTGTGGTGG ATGTGAGATC
CTCACCATAG GGAGGAGATT AGGGTCTGTG CTCAGGGCTG GGGAGAGGTG
CCTGGATTTC TCTTTGATGG GGATGTTGGG GTGGGAATCA CGATACACCT
GATCAGCTGG GTGTATTTCA GGGATGGGGC AGACTTCTCA GCACAGCACG
GCAGGTCAGG CCTGGGAGGG CCCCCCAGAC CTCCTTGTCT CTAATAGAGG
GTCATGGTGA GGGAGGCCTG TCTGTGCCCA AGGTGACCTT GCCATGCCGG
TGCTTTCCAG CCGGGTATCC ATCCCCTGCA GCAGCAGGCT TCCTCTACGT
GGATGTTAAA GGCCCATTCA GTTCATGGAG AGCTAGCAGG AAACTAGGTT
TAAGGTGCAG AGGCCCTGCT CTCTGTCACC CTGGCTAAGC CCAGTGCGTG
GGTTCCTGAG GGCTGGGACT CCCAGGGTCC GATGGGAAAG TGTAGCCTGC
AGGCCCACAC CTCCCCCTGT GAATCACGCC TGGCGGGACA AGAAAGCCCA
AAACACTCCA AACAATGAGT TTCCAGTAAA ATATGACAGA CATGATGAGG
CGGATGAGAG GAGGGACCTG CCTGGGAGTT GGCGCTAGCC TGTGGGTGAT
GAAAGCCAAG GGGAATGGAA AGTGCCAGAC CCGCCCCCTA CCCATGAGTA
TAAAGCACTC GCATCCCTTT GCAATTTACC CGAGCTCTGT CCTTCTGCCA
                                  Sac I
TGGCCCTGTG GATGCGCCTC CTGCCCCTGC TGGCGCTGCT GGCCCTCTGG
GGACCTGACC CAGCCGCAGC CTTTGTGAAC CAACACCTGT GCGGCTCACA
                                  B chain
CCTGGTGAAG CTCTCTACCT AGTGTGCGGG GAACGAGGCT TCTTCTACAC
ACCCAAGACC CGCCGGGAGG CAGAGGACCT GCAGGGTGAG CCAACCGCCC
                C chain
ATTGCTGCCC CTGGCCGCCC CCAGCCACCC CCTGCTCCTG GCGCTCCCAC
CCAGCATGGG CAGAAGGGGG CAGGAGGCTG CCACCCAGCA GGGGGTCAGG
TGCACTTTTT TAAAAAGAAG TTCTCTTGGT CACGTCCTAA AAGTGACCAG
CTCCCTGTGG CCCAGTCAGA ATCTCAGCCT GAGGACGGTG TTGGCTTCCG
                                                     G
GCAGCCCCGA GATACATTAG AGGGTGGGCA CGCTCCTCCC TCCACTCGCC
                    C
CCCCTCAAAC AAATGCCCCG CAGCCCATTT CTCCACCCTC ATTTGATGAC
CGCAGATTCA AGTGTTTTGT TAAGTAAAGT CCTGGGTGAC CTGGGGTCAC
AGGGTGCCCC ACGCTGCCTG CCTCTGGGCG AACACCCCAT CACGCCCGGA
GGAGGGCGTG GCTGCCTGCC TGAGTGGGCC AGACCCCTGT CGCCAGGCCT
CACGGCAGCT CCATAGTCAG GAGATGGGGA AGATGCTGGG GACAGGCCCT
GGGGAGAAGT ACTGGGATCA CCTGTTCAGG CTCCCACTGT GACGCTGCCC
CGGGGCGGGG GAAGGAGGTG GGACATGTGG GCGTTGGGGC CTGTAGGTCC
ACACCCAGTG TGGGTGACCC TCCCTCTAAC CTGGGTCCAG CCCGGCTGGA
GATGGGTGGG AGTGCGACCT AGGGCTGGCG GGCAGGCGGG CACTGTGTCT
CCCTGACTGT GTCCTCCTGT GTCCCTCTGC CTCGCCGCTG TTCCGGAACC
TGCTCTGCGC GGCACGTCCT GGCAGTGGGG CAGGTGGAGC TGGGCGGGGG
                                    C chain
CCCTGGTGCA GGCAGCCTGC AGCCCTTGGC CCTGGAGGGG TCCCTGCAGA
AGCGTGGCAT TGTGGAACAA TGCTGTACCA GCATCTGCTC CCTCTACCAG
        A chain
CTGGAGAACT ACTGCAACTA GACGCAGCCT GCAGGCAGCC CCACACCCGC
CGCCTCCTGC ACCGAGAGAG ATGGAATAAAGCCCTTGAACCAGCCCTGC
                            ◄———————— INSULIN 3'primer
```

RECOMBINANT VECTOR FOR USE IN GENE THERAPY FOR INSULIN-DEPENDENT DIABETES MELLITUS AND THERAPEUTIC COMPOSITION THEREOF

BACKGROUND OF THE INVENTION

The present invention relates to a recombinant vector suitable for use in gene therapy for insulin-dependent diabetes mellitus and a pharmaceutical composition comprising the recombinant vector as an effective ingredient. More particularly, the present invention relates to a gene therapy system for effectively and safely treating insulin-dependent diabetes mellitus by taking advantage of the gene delivery capacity of Drosophila's P-transposon and the tissue specificity and expression enhancement of a K14 promoter.

Gene therapy offers a new paradigm for curing human diseases. Rather than altering disease phenotypes by using agents that interact with gene products or are themselves gene products, gene therapy theoretically can modify specific genes, which results in a cure following a single administration. Initially, gene therapy was envisioned for the treatment of genetic disorders, but is currently studied for a broad spectrum of diseases, including cancer, peripheral vascular disease, arthritis, neuro-degenerative disorders and other acquired diseases. Further, in combination with the Human Genome Project, gene therapy is expected to make a great progress in the treatment of far more diseases. With gene therapy, the delivery of genes into cells and their expression therein can be artificially regulated, so that the mutated genes of patients can be corrected by genetic recombination.

There are disclosed patents regarding gene therapy. For instance, PCT publication No. 1997-27310 claims a retrovirus vector which can be used in gene therapy and PCT publication No. 1997-34009 discloses a recombinant adenovirus vector for gene therapy for human tumors. Virus vectors are, however, limited to only the treatment of hereditary diseases, owing to safety concerns and highly complex procedures. Also, the gene therapy utilizing virus vectors, as in such patents, suffers from the disadvantage of requiring much time and high expense. In prior arts, non-viral insulin vectors have been disclosed nowhere yet.

Characterized by a grossly abnormal pattern of fuel usage-overproduction of glucose by the liver and under utilization by other organs, diabetes mellitus is a metabolic disease caused by insulin deficiency. Of various diabetes mellitus patterns, Insulin-dependent diabetes mellitus (IDDM), called Type I diabetes, results from the autoimmune destruction of the insulin-producing β-cells of the pancreas. Currently, IDDM accounts for 3% of all new cases of diabetes each year with one incidence per 7,000 children.

Measures in current use for the treatment of IDDM include the monitoring of blood sugar levels, multiple injections of insulin, specialized diet, and exercise. In spite of faithful compliance with such intensive diabetes management strategies, patients can expect only a 50–70% reduction in the aggravation of diabetes. Therefore, there remains a need for developing better therapies.

The epidermis and its appendages, which are self-renewing tissues, have compartments of stem cells, each having the capacity to proliferate sufficiently to cover the body surface. The pioneering studies of Green et al. (1983) established that human skin keratinocytes could be serially propagated in culture for several hundred generations, resulting in the development of burn grafting operations employing cultured skin keratinocytes, which are now widely used in trauma units of major hospitals. Gene transfer into cultured keratinocytes has been demonstrated by utilizing a variety of different foreign promoters able to drive the expression of various secreted products. Keratinocytes within the epidermis are renewed by replicating cells which fall within the following two categories: (1) stem cells capable of extended or unlimited growth; and (2) transient amplifying cells, descended from stem cells, that replicate a limited number of times before undergoing terminal differentiation. Stem cells show slow cell cycles and are labeled infrequently with nucleotide analogues, but once labeled, retain that label for prolonged time periods. Stem cells and transient amplifying cells are located in compartments in the basal layer of the epidermis with terminally differentiated cells forming the stratified, super-basal layers. A stem cell and its descendant amplifying and terminally differentiated cells are clustered in a distinct spatial array termed the 'epidermal proliferation unit'. Keratin 14 (K14) and its partner K5 are the major proteins expressed by active cells of the epidermis and its appendages, and the genes encoding these keratins are abundantly transcribed in cultured human keratinocytes. For these reasons, the K14 and K5 promoters are especially attractive candidates for use in keratinocyte-mediated gene therapy.

Since the first finding in the 1970s that P-transposon is included in the hybrid dysgenesis, Drosophila's P-element has been under extensive study. A technique was reported in which cloned genes can be transferred to Drosophila's embryos by use of P-transposon (Rubin, G. M., et al., Science, 1982, 218:348–353). However, this technique is not applicable even to allied species. Furthermore, the introduction of Drosophila's transposon to mammals, as in the present invention, has not yet been reported thus far.

SUMMARY OF THE INVENTION

Leading to the present invention, the intensive and thorough research on gene therapy, conducted by the present inventors aiming to develop more effective, safer and simpler gene therapy for type I diabetes mellitus, resulted in the finding that a K14 promoter gene designed to govern the expression of a human insulin gene shows such tissue specific enhancement activity that the human insulin gene can be integrated to the chromosome of keratinocytes with the aid of Drosophila's transposase, and insulin can be produced by the keratinocytes in a quantity sufficient to maintain normal blood glucose levels.

Therefore, it is an object of the present invention to provide a non-viral, recombinant insulin expression vector suitable for use in gene therapy for diabetes mellitus.

It is another object of the present invention to provide a non-viral vector containing a DNA sequence coding for Drosophila's P-transposon, suitable for use in gene therapy.

It is a further object of the present invention to provide use of the non-viral, recombinant insulin expression vector in treating diabetes mellitus.

It is still a further object of the present invention to provide use of the non-viral vector containing a DNA sequence coding for Drosophila's p-transposon in integrating genes to mammalian chromosomes.

It is still another object of the present invention to provide use of the non-viral vector containing a DNA sequence coding for Drosophila's P-transposon in treating diabetes mellitus.

It is yet another object of the present invention to provide a method for treating diabetes mellitus by gene therapy.

It is yet a further object of the present invention to provide a composition for gene therapy for insulin-dependent diabetes mellitus, which is safe and easy to apply to humans.

BRIEF DESCRIPTION OF THE DRAWINGS

FIG. 7 is a base sequence encoding a K14 promoter and a human insulin, harbored in the insulin expression plasmid vector, pUCK14-INS.

DETAILED DESCRIPTION OF THE INVENTION

The present invention pertains to a gene therapy system capable of delivering a gene of interest to a mammalian chromosome. Particularly, the gene therapy system is useful for curing insulin-dependent diabetes mellitus. To approach this aim, advantage is taken of the tissue specificity and enhancement activity of a K14 promoter in integrating a gene of interest into the chromosome of a targeted tissue. Also, Drosophila's P-transposon is utilized in the chromosomal integration of a gene in accordance with the present invention.

Therefore, the integration of a gene into the chromosome of a targeted tissue is achieved by the cooperation of the tissue specificity of the K14 promoter and the enzymatic activity of the transposase. To verify the chromosomal integration, a β-galactosidase gene is selected as a reporter gene because the expression of β-galactosidase can be easily seen by X-gal staining.

Figure 1A:
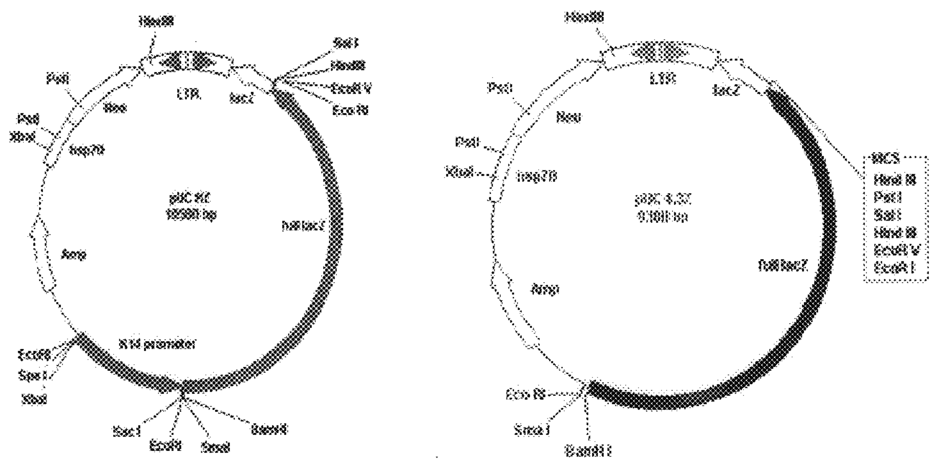
FIG. 1*a* shows schematic diagrams of β-galactosidase expression plasmid vectors having a complete lacZ gene with a K14 promoter (left, pUC KZ) and with no K14 promoter (right, pUC 4.3Z).
Figure 1B:
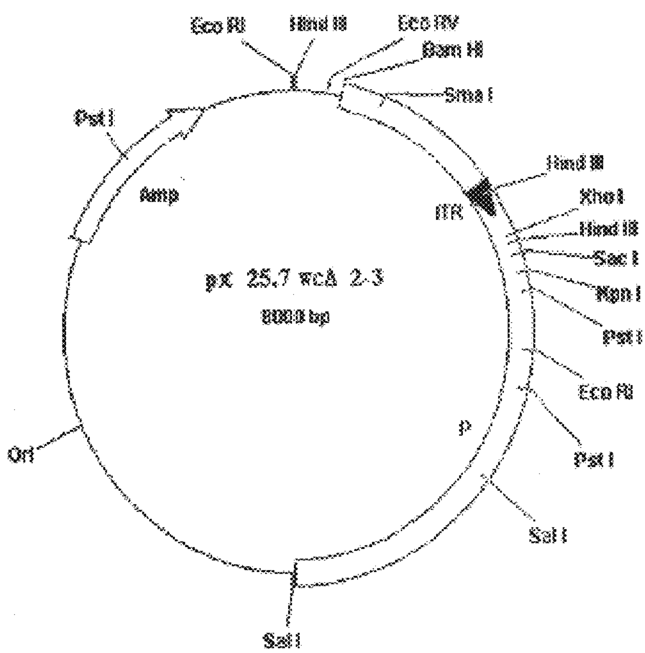
FIG. 1*b* is a schematic diagram showing a helper plasmid vector (pπ25.7wcΔ2–3) capable of expressing Drosophila's P-transposase.

First, two mammalian expression plasmids are constructed: one containing a lacZ gene connected to a human K14 promoter gene; and the other containing a lacZ gene without a K14 promoter gene, as shown in FIG. 1*a*. In this regard, a human K14 promoter gene is inserted at the EcoR I site in pUChsneo and then, a 4.3 kb lacZ gene obtained from cpwβ-22 is inserted between BamH I and Sal I in the same plasmid. The resultant plasmid is called pUC KZ. Separately, a lacZ gene of the same length is inserted into pUChsneo. This recombinant plasmid is called pUC 4.3Z. After transfection into *E. coli* by electroporation, the plasmid DNAs are prepared and digested with restriction enzymes to confirm the subcloning of the genes. Also, a P-element transposase gene is inserted into the intron between ORF2 and ORF3 of pπ25.7wcΔ2–3, as shown in FIG. 1*b*, to construct a helper vector capable of allowing the genes of interest to integrate into the chromosome.

Next, mammalian transfection requires a large concentration of highly pure plasmid DNA. A commercially available plasmid DNA preparation kit, for example, QIAGEN plasmid maxi kit (QIAGEN GmbH, Germany), is useful for this end. In the present invention, the mammalian transfection is achieved by liposome mediation. Reagents suitable for this liposome-mediated gene delivery can also be purchased, for example, GenePORTER™ transfection reagent (GTS Inc., San Diego, Calif., U.S.A.). Before use, this reagent is hydrated with 0.75 ml of a hydration buffer at room temperature and vortexed. Various concentrations of plasmid DNAs are combined with various volumes of the reagent to prepare DNA/liposome complexes. To the complexes, the helper vector is added at an amount of 40% weight/volume of the diluted DNA solutions, followed by the addition of one volume of GenePORTER™. The resulting solution is added with PBS to the final volume of 130 μl and incubated at room temperature for 30 min just before use.

To mice 10–12 weeks old, various concentrations of the DNA/liposome complexes are administered through pressure injection using a needle-less jet injector, such as that manufactured by Mada Medical Products, Inc. The administered mice are sacrificed by cervical dislocation from one day to 20 weeks after the DNA application and samples are immediately obtained from the skin areas where the DNA was injected.

To visualize the expression of the lacZ gene in the skin tissue, the tissue samples are soaked in an X-gal solution. Before the X-gal staining, the tissue samples are washed with PBS and fixed in a fixative. The X-gal solution is preferably prepared just before use.

Afterwards, the skin samples which appear as different shades of blue as stained in X-gal are washed twice with PBS, followed by fixation in formalin. The fixation is to preserve the morphology of the living tissue for hematoxylin/eosin staining. Formalin, one of the most popular fixatives, serves to crosslink nucleic acids to proteins, thus making the molecules rigid and susceptible to mechanical shearing. The duration of the fixation preferably ranges from 16 hours to 3 days. Then, a routine H/E staining method is applied to the fixed tissue samples. In this regard, paraffin embedding, sectioning and mounting of the tissue samples are conducted. Preferably, the tissue samples are mounted as close to the center of the slide as possible. Sections are required to be thinner than 10 μm because thicker sections are difficult to visualize.

The integration of the lacZ gene into the chromosome of the targeted tissue is confirmed by PCR screening and Southern blot analysis.

For this, genomic DNA is first prepared from the murine skin region (diameter 2 cm) where the vectors are injected. Murine skin is dissected out and minced well in a tail tip buffer (60 mM Tris pH 8.0, 100 mM EDTA, 0.5% SDS) using curved scissors. After treatment with RNase A and Proteinase K, the murine skin sample is centrifuged. From the supernatant, genomic DNA is precipitated by a phenol extraction method.

A PCR is carried out using the genomic DNA as a template. In order to detect a lacZ region, the primers can be made from *E. coli* HB101 including a lacZ gene. Its product length is expected to be 3,110 bp.

In the same manner as in above, genomic ENAs are prepared from vector-injected ventral areas that are marked at the time the vector is applied. The genomic DNAs are electrophoresed on an agarose gel in 1×TAE buffer and transferred to a membrane which is then dried at 80° C. for 2 hours. The transferred DNAs are allowed to hybridize with a [α—$^{32}$P]dCTP-labeled probe in a hybridization buffer (5×SSC, 1/20 diluted liquid block, 0.1% SDS, 5% dextran sulphate). Next, the membrane is washed many times with washing buffers and subjected to autoradiograph analysis.

In the above experiments, it was found that the lacZ gene is firmly integrated into the chromosome of keratinocytes and expressed strongly by the cooperative activities of Drosophila's P-transposase and K14 promoter.

These promising results were also found to be true when a human insulin gene was studied.

In order to construct an insulin expression plasmid vector containing a K14 promoter gene, two pairs of PCR primers are made with known base sequences of a human preproinsulin gene and a K14 promoter region and used to amplify the genes by PCR with human genomic DNA serving as a template. The two PCR products, preproinsulin gene and the K14 promoter gene are in tandem inserted into pUChsneo at the Sal I site. The resulting insulin expression vector is called pUCK14-INS.

The insulin expression recombinant vector pUCK14-INS was deposited in the Korean Collection for Type Culture of Korea Research Institute of Bioscience and Biotechnology (KRIBB) under the deposition No. KCTC 0928P on Jan. 10, 2001.

To confirm the cloning of the genes, the insulin expression vector is amplified and base-sequenced using ABI Prism 377 XL (PE, U.S.A.).

To make mice diabetic, streptozotocin (STZ) is administered at doses of 65 mg/kg and 200 mg/kg ten times in total. Blood glucose levels can be determined using a Super Glucocard™ KIT (Arkray KDK Corp., Kyoto, Japan). A drop of sample blood obtained from the tail is placed on the tip of the Glucocard test strip. The strip's reaction chamber automatically draws the blood inside the strip through capillary action. When the chamber is full, the Glucocard kit starts to measure the blood glucose level. The glucose in the sample reacts with the glucose oxidase and potassium ferricyanide in the strip, producing potassium ferrocyanide in proportion to the glucose concentration of the blood sample. Oxidation of the potassium ferrocyanide produces an electrical current, which is then converted by the meter to display the glucose concentration.

For immunostaining pancreatic β-cells, 6 mice (one normal mouse, 2 diabetic mice to which STZ was injected at doses of 65 mg/kg and 200 mg/kg, and 3 mice to which the insulin expression vector was injected at doses of 1 μg, 50 μg and 100 μg) were sacrificed by cervical dislocation and their pancreases were collected and fixed in a 10% formalin fixative. In order to visualize the distribution of Langerhans islets in the normal pancreases and diabetic pancreases by H/E staining, paraffin embedding, sectioning and mounting of the tissues samples were conducted as in above. Quantitative analysis of the insulin producing ability of β-cells was achieved by using antibodies, including an anti-insulin Ab, an anti-glucagon Ab, and anti-somatostatin Ab.

A better understanding of the present invention may be obtained in light of the following examples which are set forth to illustrate, but are not to be construed to limit the present invention.

Experimental Example 1

β-Galactosidase Gene Expression in Murine Skin

First Stage: Construction of β-galactosidase Expression Vector

A human K14 promoter gene was inserted to pUChsneo at the EcoR I site, followed by the addition of 4.3 kb of a lacZ gene, obtained from cpwβ-22, to a site adjacent to the cloned K 14 promoter between the BamH I and Sal I sites of the plasmid. The resulting plasmid was termed pUC KZ and is schematically depicted in FIG. 1*a* (left). Separately, only a full length of a lacZ gene was cloned into pUChsneo to prepare pUC 4.3Z, as depicted in FIG. 1*a* (right). After the transfection into *E. coli.,* the two plasmid DNAs were purified by phenol/chloroform/isoamyl alcohol and confirmed by enzyme restriction mapping. These two plasmid DNAs harboring the lacZ gene were examined for activity of the K14 promoter.

Second Stage: Construction of Helper Vector

To compensate for the inability of pUCshneo to self-transpose into a chromosome, a helper vector was constructed, which anchored a P-element transposase gene. To this end, helper pπ 25.7wcΔ2–3 was manipulated at the intron between ORF2 and ORF3 so as to have the capacity to produce the transposase, as illustrated in FIG. 1*b*.

Third Stage: Preparation of DNA/liposome Complex

The β-galactosidase expression vector prepared in the first stage was purified by use of QIAGEN plasmid maxi kit (QIAGEN GmbH, Germany) and GenePORTER™ transfection reagent was hydrated with 0.75 ml of a hydration buffer at room temperature. Each of 2 μg, 5 μg, 10 μg, 50 μg and 100 μg of the purified plasmid DNA was combined with each of 5 μL, 10 μL and 20 μL of liposomes to prepare DNA/liposome complexes. To these diluted DNA solutions, the helper plasmid capable of expressing Drosophila's P-transposase was added at an amount of 40% w/v of the purified plasmid DNA, followed by the addition of the same volumes of GenePORTER™ transfection reagent. After dilution with a PBS reagent, the resulting solutions were incubated at room temperature for 30 min.

Fourth Stage: DNA Injection into Mouse

Mice aged 10–12 weeks with an average weight of about 26 g were administered the DNA/liposome complexes prepared in the third stage by injection into their hind legs with the aid of a needle-less jet injector (Madajet XL). The administered mice were sacrificed by cervical dislocation at predetermined time intervals from one day to 20 weeks after the DNA application and samples were collected by shaving the treated areas of the outer skin and excising out them by use of sterilized surgical scissors.

Fifth Stage: X-gal Staining

The skin samples obtained in the fourth stage were washed twice with PBS and fixed in a fixative (2% paraformaldehyde, 0.2% glutaraldehyde in 0.1 M sodium phosphate buffer, pH 7.3) for 30 min at 4° C. The samples were soaked for 3 hours at 37° C. in an X-gal solution (1.3 mM $MgCl_2$, 3 mM $K_4Fe(CN)_6$, 3 mM $Fe_3(CN)_6$, 1 mg/ml X-gal, 0.1 M sodium phosphate buffer, pH 7.3) which was prepared just before. For comparison, a control to which a solution of liposomes alone in PBS was injected, was sampled in the same manner to analyze the lacZ expression in the skin tissue.

Figure 2:
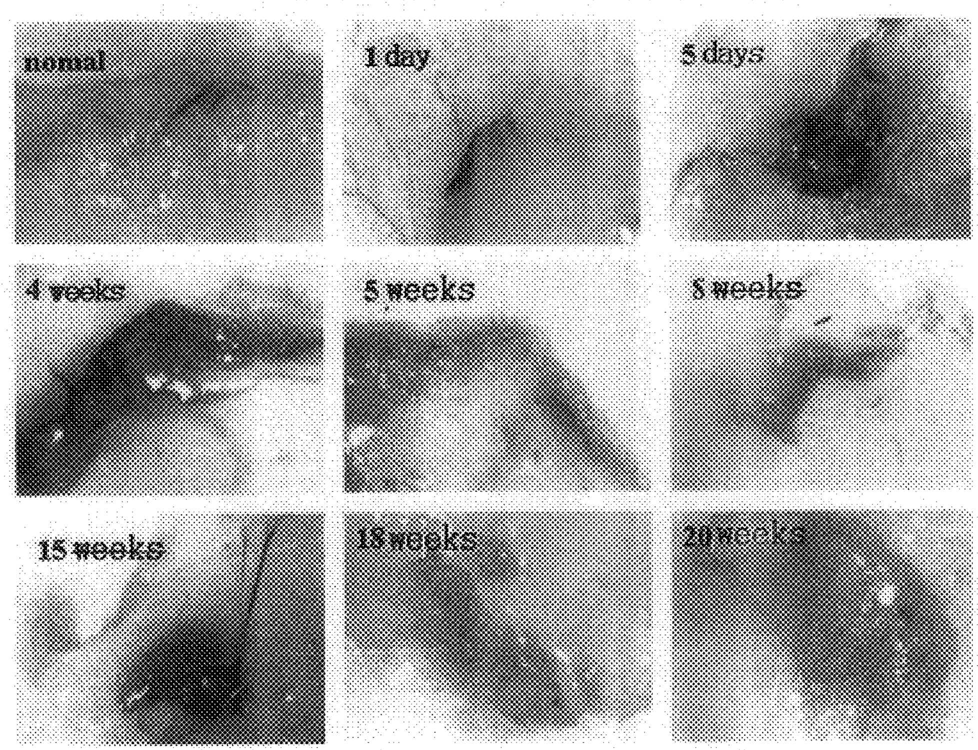
FIG. 2 shows microphotographs of murine skin tissues before and after the co-injection of pUC KZ and the helper plasmid vector. With the lapse of time (one day to 20 weeks) after the injection, the murine skin tissues appear as different blues as a result of the reaction of the β-galactosidase expressed from the plasmid in the skin tissue with X-gal.

Under a microscope, lacZ was observed to be expressed at a low level only for 5 days following the injection of the K14 promoter-deficient plasmid vector, appearing as a faint blue as stained in X-gal. In contrast, the co-injection of the pUC KZ vector having a K14 promoter region was found to enable the β-galactosidase gene to be strongly expressed, producing a deep blue for 20 weeks as stained in X-gal, as shown in FIG. 2. In addition, tissue specific enhancement of the K14 promoter enhancement was also found upon injection of the pUC KZ.

Sixth Stage: H/E (Hematoxylin/Eosin) Staining

Skin samples which reacted in the X-gal solution to express blue spots were washed twice with PBS and fixed in formalin for H/E (hematoxylin/eosin) staining. Following fixation for 16 hours to 3 days, a routine H/E staining method was conducted with sections of a thickness lower than 10 μm.

Figure 3:
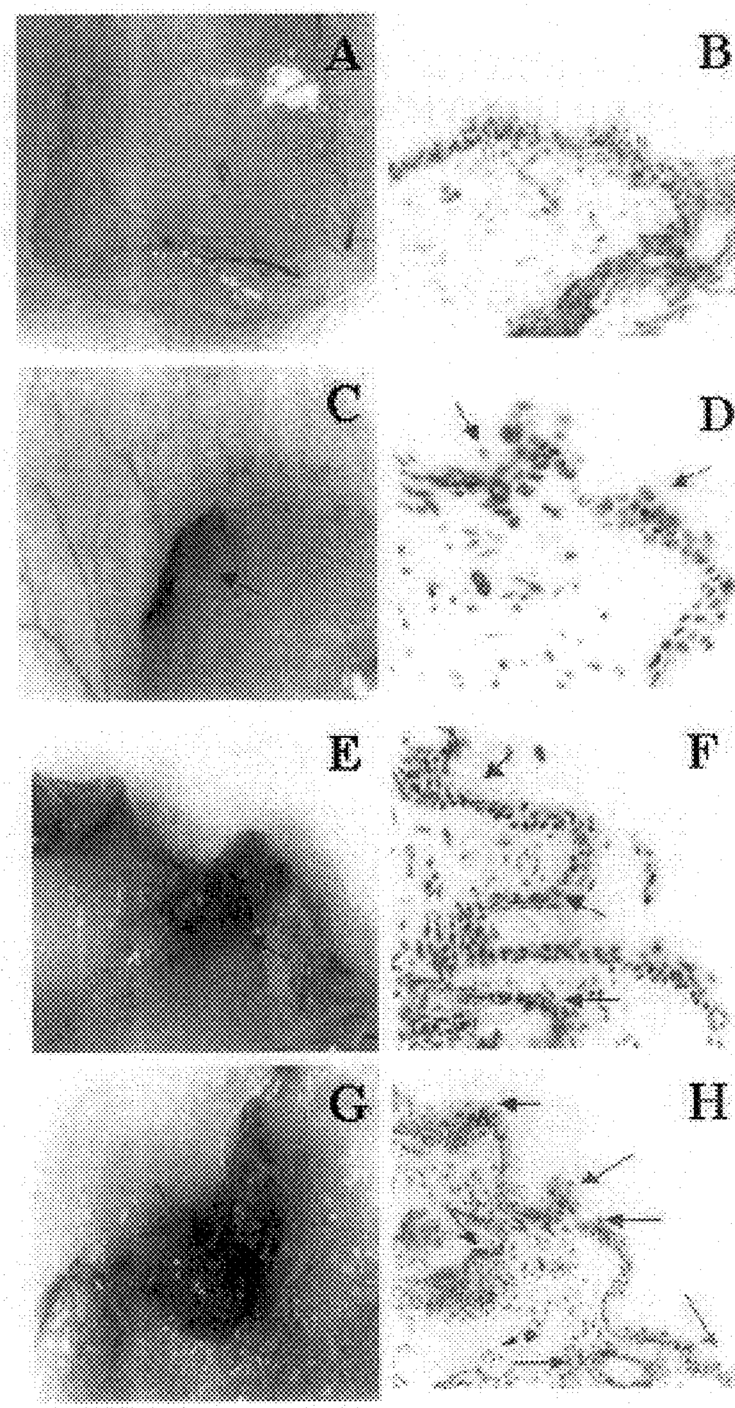
FIG. 3 shows microphotographs of murine skin tissues before and after the co-injection of pUC KZ and the helper plasmid vector, which are stained with X-gal (left column: A, C, E, G) or with hematoxylin/eosin (right column: B, D, F, H). Compared with the normal skin tissues (top panel), the co-injected skin tissues are observed to accumulate more β-galactosidase with the lapse of time (one day: second panel, one week: third panel, and four weeks: bottom panel) after the co-injection, as demonstrated by X-gal staining. The H/E staining elucidates clearly that the cells in which the β-galactosidase gene is expressed are keratinocytes. In the photographs, arrows indicate the expression of β-galactosidase.

Results are shown in FIG. 3. Blue spots or diffused forms of X-gal reactants were found around nuclei in all sample tissues. Also, as seen in FIG. 3, intense expression of the β-galactosidase gene was found in the keratinocyte layer as a result of the tissue specificity, and sustained from 4 days to 5–6 weeks after the injection.

Seventh Stage: Preparation of Mouse Genomic DNA

Murine skin was dissected and minced well in a small volume puddle of tail tip buffer (60 mM Tris pH 8.0, 100 mM EDTA, 0.5% SDS). After addition of 600 μl of the tail tip buffer and treatment with RNase A (20 m./ml), incubation was conducted at 37° C. for 30 min. Proteinase K was added at a concentration of 500 μg/ml and reacted at 50–55° C. This reaction was centrifuged at 1,200 rpm at 20° C. for 15 min and the resulting three layers were deprived of the middle layer before re-centrifugation. After extraction with phenol/chloroform three times and with chloroform once, the supernatant was centrifuged at 20° C. at 10,000 rpm for 15 min. To the separated aqueous phase, 1/10 volume of 3 M NaOAc, pH 5.2, and an equal volume of 95% EtOH was added to precipitate DNA. The dried pellet was re-dissolved in a TE buffer (pH 7.4) and the O. D. of the 1/5000 dilution of the TE solution was read at 260 nm.

Eighth Stage: PCR Screening for Confirmation of the Chromosomal Integration of β-galactosidase Gene Genomic DNA was purified in the same manner as in the seventh stage from murine skin samples taken from the injected regions (diameter 2 cm) 5 days to 4 weeks after injection. In order to confirm the integration of the β-galactosidase gene in the chromosome after injection, the following primers were synthesized with a design to produce a 3110 bp PCR product. The PCR was carried out under the conditions described in Table 1, below.

```
                                         SEQ ID NO:1
lacZ forward- 5' TCACTCTAGAAACAGCTATGA3'
                                         SEQ ID NO:2
lacZ reverse- 5' TCGACCCGGTTATTATTA3'
```

TABLE 2

PCR condition for lacZ amplification in genomic DNA.

| PCR Composition | |
|---|---|
| Primers | 10 pmol (lac5', lac3') |
| Expected length of PCR Product | 3110 bp |
| Reaction volume | 20 μl |
| Ex Taq | 0.5 unit |
| 10x Ex Taq buffer | 2 μl |
| Template DNA Concentration | 50 pmol |
| DNTPs | 200 pmol |

| PCR Temp. and Time | 1 Cycle | 35 Cycles | 1 Cycle |
|---|---|---|---|
| Denaturation | 90° (180 sec) | 94° (30 sec) | 94° (60 sec) |
| Annealing | 52° (60 sec) | 52° (60 sec) | 52° (60 sec) |
| Extension | 72° (60 sec) | 72° (60 sec) | 72° (60 sec) |

Figure 4:
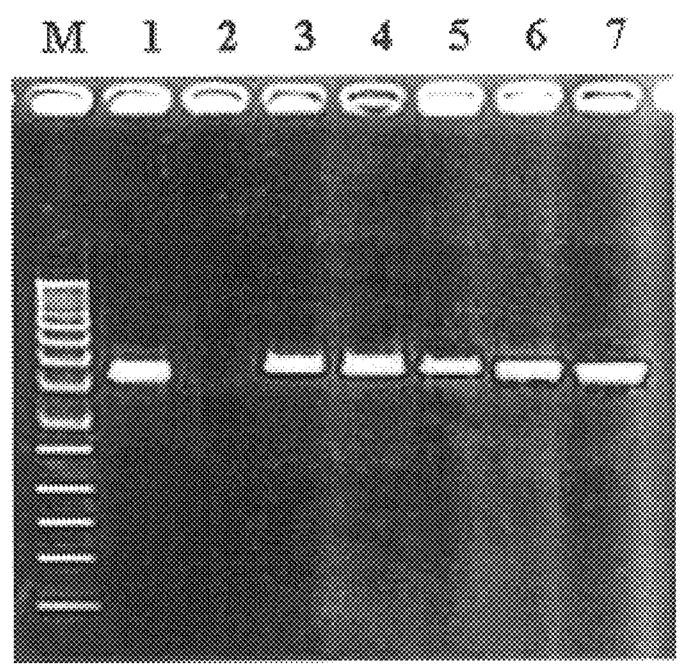
FIG. 4 is a photograph of an agarose gel on which PCR products were run. The PCR products were amplified from genomic DNAs prepared 5 days (lane 3), one week (lane 4), two weeks (lane 5), three weeks (lane 6) and four weeks (lane 7) after the co-injection of pUC KZ and the helper vector. The PCR products were electrophoresed, along with pUC KZ as a positive control (lane 1), a genomic DNA as a negative control (lane 2), and a marker (M), so as to demonstrate the integration of the β-galactosidase gene into the chromosome by the enzymatic action of the transposase.

PCR products which were amplified from 5 samples respectively taken 5 days, 1 week, 2 weeks, 3 weeks and 4 weeks after the injection of the vector in which a β-galactosidase gene was harbored, were all found to be about 3100 bp long as measured by gel electrophoresis. The electrophoresis data shown in FIG. 4 demonstrated the insertion of the β-galactosidase gene into the chromosome.

Ninth Stage: Southern Blotting for Confirmation of the Chromosomal Integration of the β-galactosidase Gene For use in Southern blotting analysis, genomic DNA was purified in the same manner as in the seventh stage from mice to which β-galactosidase expression vector was injected. For comparison, genomic DNA samples which were prepared from the mock-treated mice and pUC KZ-injected mice were used as a negative and a positive control, respectively.

The genomic DNAs were run on 0.8% agarose gel in 1×TAE buffer by electrophoresis and the separated DNAs were transferred to a Hybond $N^+$ membrane. After being baked at 80° C. for 2 hours, the blotted DNAs were hybridized with a [$\alpha$-$^{32}$P]dCTP-labeled probe in a hybridization buffer (5×SSC, 1/20 diluted liquid block, 0.1% SDS, 5% dextran sulphate) Next, the membrane was washed with a washing buffer (2×SSC, 0.1% SDS) at 42° C. for 10 min, then with a buffer (1×SSC, 0.1% SDS) at 42° C. for 10 min, and finally twice with a buffer (1×SSC, 0.1% SDS) at 65° C. for 10 min.

Figure 5:
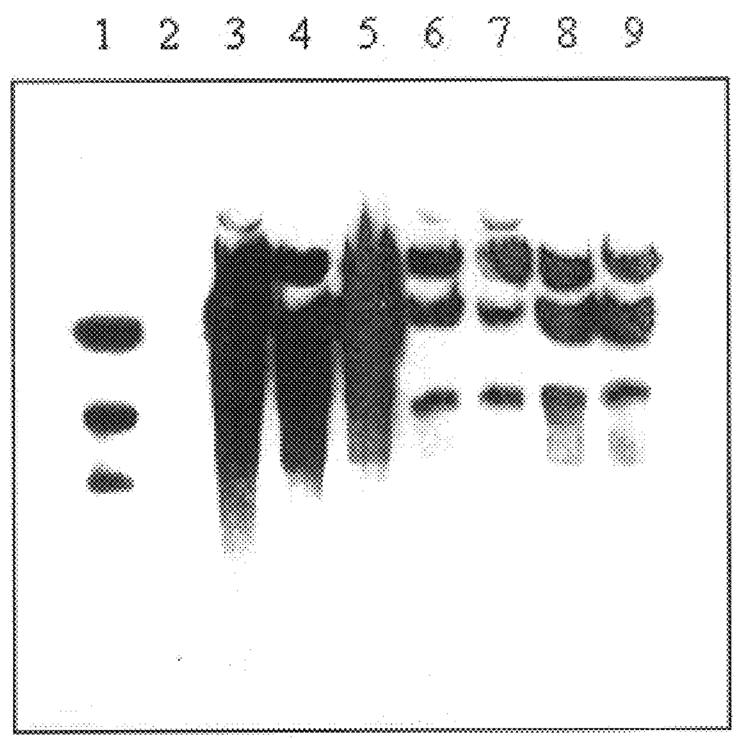
FIG. 5 is a Southern blot autoradiogram showing the chromosomal integration of the β-galactosidase gene in the targeted murine tissue. Genomic DNAs were prepared from skin samples at five days (lane 3), one week (lane 4), two weeks (lane 5), three weeks (lane 6), four weeks (lane 7), five weeks (lane 8) and six weeks (lane 9) after the co-injection of pUC KZ and the helper plasmid vector. For comparison, 200 ng of pUC KZ was loaded as a positive control (lane 1) and genomic DNA prepared from a non-injected normal murine skin sample was used as a negative control (lane 2).
Figure 6:
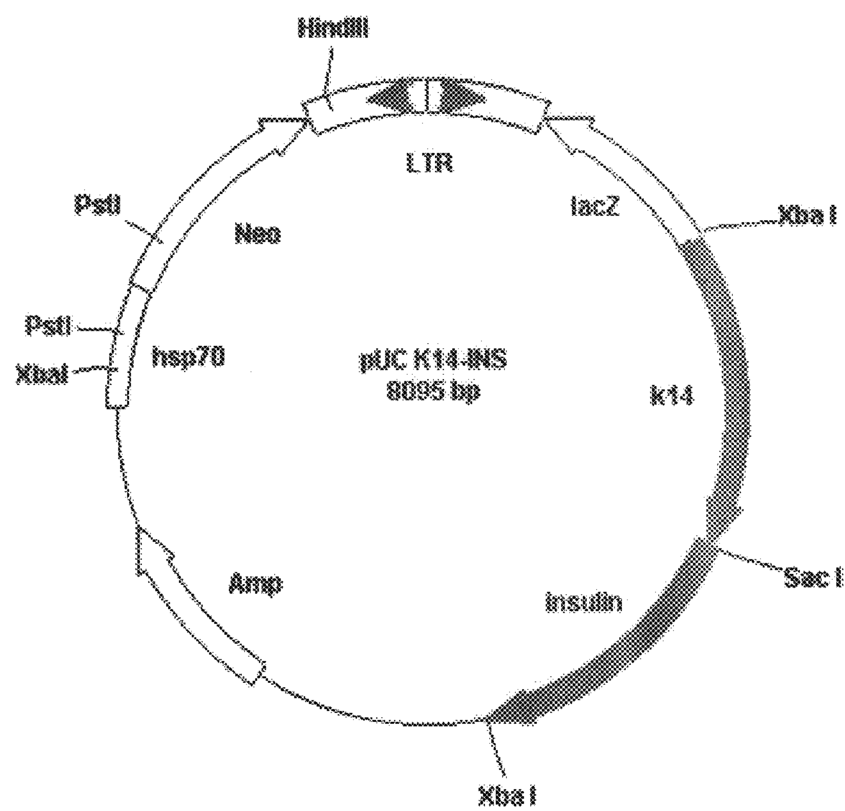
FIG. 6 is a schematic diagram showing the insulin expression plasmid vector of the present invention, pUCK14-INS.

Autoradiographic analysis is given in FIG. 5. As seen in the autoradiogram, although bands were not clear in lanes for the samples obtained from mice sacrificed 5 days and 1 week post-administration, the β-galactosidase gene was successfully integrated into the murine chromosome by the enzymatic activity of the transposase expressed from the co-injected helper vector as demonstrated by the clear bands for the genomic DNAs obtained 2 to 5 weeks post-administration.

EXAMPLE 1

Construction of Insulin Vector

Two pairs of PCR primers were designed by taking advantage of known base sequences of a human preproinsulin gene and a K14 promoter region, as shown in Table 1, below, and used to amplify the genes by PCR. The two PCR products, preproinsulin gene and the K14 promoter gene, were sub-cloned into pUChsneo and pGEM T-easy, respectively, followed by inserting them in tandem into pUChsneo at the Sal I site. The resulting insulin expression vector was called PUCK14-INS.

TABLE 2

PCR Primers for Insulin Gene and K14 Promoter

| Primers | Sequence |
|---|---|
| Insulin forward | 5' CCTGCCTGTCTCCCAGAGCTCTGTCCTTCT3' SEQ ID NO. 3 |
| Insulin reverse | 5' GCAGGGCTGGTTCTAGAGCTTTATTCCATC3' SEQ ID NO. 4 |
| K14 promoter Forward | 5' ATTGCTGAAGTTTTGATCTAGACACCTCCA3' SEQ ID NO. 5 |
| K14 promoter reverse | 5' CTGAGTGAAGAGAAGGAGCTCGGGTAAATT3' SEQ ID NO. 6 |

The insulin expression recombinant vector pUCK14-INS was deposited in the Korean Collection for Type Culture of Korea Research Institute of Bioscience and Biotechnology (KRIBB) under the deposition No. KCTC 0928P on Jan. 10, 2001.

EXAMPLE 2

Base Sequence Analysis of Insulin Expression Vector

The insulin expression vector prepared in Example 1 was purified with the aid of QIAGEN plasmid mini (QIAGEN, Valencia, Calif., U.S.A.) and subjected to sequence analysis using ABI Prism 377 XL (PE, U.S.A.). The base sequences of the K14 promoter and the preproinsulin gene are given in FIG. 7. As seen, the K14 promoter region is connected at a Sac I site to the insulin gene which consists of three insulin peptide parts, proinsulin peptide B, proinsulin peptide C and proinsulin peptide A, and a 790 bp intron in the C-chain.

EXAMPLE 3

Induction of Diabetes Mellitus in Mice and Change in Blood Glucose Level Upon Administration of Insulin Expression Vector Streptozotocin (STZ) was administered at doses of 65 mg/kg and 200 mg/kg ten times in total to mice by hypodermic injection to induce diabetes mellitus. For use, STZ was dissolved in cold 0.1 M citrate buffer (pH 4.5) immediately before the injection. 4 days after every STZ injection, the insulin expression vector was injected at doses of 1 $\mu$g, 2 $\mu$g, 3 $\mu$g, 10 $\mu$g, 50 $\mu$g and 100 $\mu$g to the diabetes mellitus-induced groups, each consisting of four mice. The STZ and the insulin expression vector were injected alternately once every four days. The progression of diabetes mellitus was monitored by blood glucose analysis.

Blood glucose levels were measured using a Super Glucocard™ II kit (Arkray KDK Corp., Kyoto, Japan). In this regard, blood samples were taken from tails and one drop of the blood was placed on the tip of the Glucocard test strip.

Figure 8A:
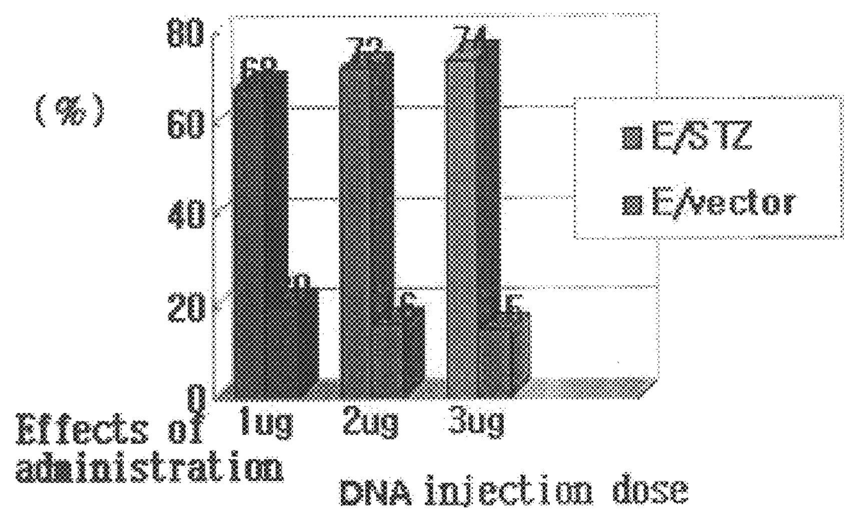
FIG. 8 shows histograms in which blood glucose levels of mice are measured according to administration doses of pUCK14-INS after the induction of diabetic mellitus in the mice by the treatment with streptozotocin at a dose of 65 mg/kg (a) and at a dose of 200 mg/kg (b).
Figure 8B:
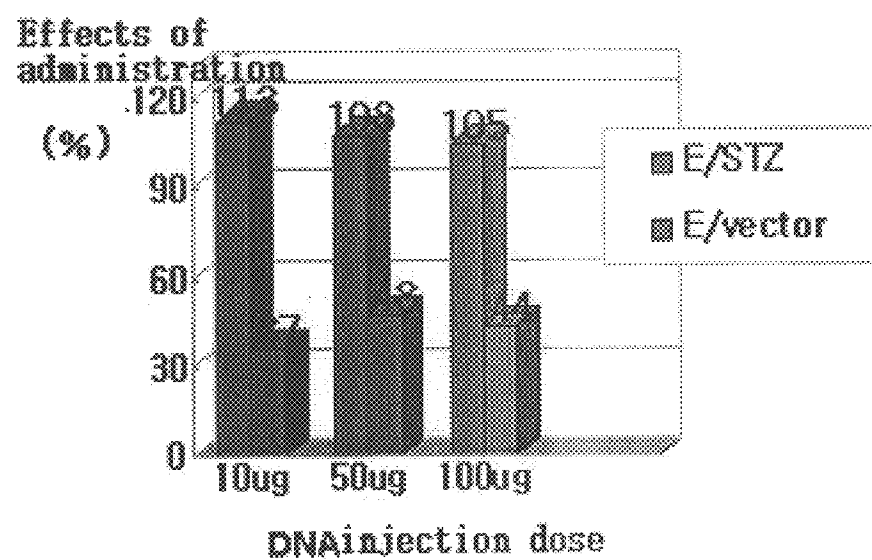

As a result of monitoring every two hours, normal blood glucose levels were measured to range from 65 mg/dl to 145 mg/dl throughout one day with an average of 105 mg/dl. Measurements of blood glucose levels after every injection and administration are given in Tables 3 to 5, below and drawn in FIGS. 8*a* and 8*b*.

As seen, the insulin expression vector decreased the blood glucose levels in a dose-dependent pattern. The alternating treatment with insulin expression vector and STZ resulted in the fluctuation of blood glucose levels. However, blood glucose level increments at later rounds of the alternating treatment with 65 mg/kg of STZ and the insulin expression vector were reduced compared with initial rounds, while the decreasing effect of the insulin expression vector on the blood glucose level was continuously maintained throughout the treatment. The mouse group which was administered STZ at a dose of 200 mg/kg showed hyperglycemia within a relatively short period of time. In this case, the injection of the insulin expression vector resulted in a decrease in blood glucose level in a dose-dependent pattern, as well.

TABLE 3

| Blood Glucose Levels of Diabetic Mice, Caused by STZ | | |
|---|---|---|
| Dose (mg/kg) | Injection Round | Blood Glucose (mg/dl) |
| 65 | 0 | 105 |
| 65 | 1, 2 | 119, 128 |
| 65 | 3.4.5 | 130, 238, 280 |
| 65 | 6 | 320 |
| 65 | 10 | >600 |
| 200 | 0 | 105 |
| 200 | 1, 2 | 339, 448 |
| 200 | 3.4.5 | 574, 600, >600 |
| 200 | 6 | >600 |
| 200 | 10 | >600 |

TABLE 4

Change in Blood Glucose Level of Diabetic Mice Treated with 65 mg/kg of STZ

| Blood Glucose | Blood Glucose After Treatment with Insulin Expression Vector (mg/dl) | | |
|---|---|---|---|
| Before Treatment (mg/dl) | 1 μg | 2 μg | 3 μg |
| 150 | 116 | 147 | 121 |
| 200 | 148 | 99 | 114 |
| 300 | 105 | 121 | 263 |
| 400 | 196 | 204 | 215 |
| 500 | 207 | 245 | 234 |
| 600 | 328 | 342 | 344 |

TABLE 5

Change in Blood Glucose Level of Diabetic Mice Treated with 200 mg/kg of STZ

| Blood Glucose | Blood Glucose After Treatment with Insulin Expression Vector (mg/dl) | | |
|---|---|---|---|
| Before Treatment (mg/dl) | 10 μg | 50 μg | 100 μg |
| 150 | 76 | 62 | 61 |
| 200 | 138 | 99 | 68 |
| 300 | 58 | 182 | 108 |
| 400 | 293 | * | * |
| 500 | 300 | * | * |
| 600 | 375 | * | * |

* blood glucose levels were sustained in the range of 85–120 mg/dl and did not exceed 320 mg/dl.

EXAMPLE 5

Immunohistochemistry of Langerhans islets

A normal mouse, and 2 diabetic mice to which STZ were injected at doses of 65 mg/kg and 200 mg/kg, and 3 mice to which the insulin expression vector was injected at doses of 1 μg, 50 μg and 100 μg, were sacrificed by cervical dislocation and their pancreases were collected and fixed in a 10% formalin fixative. For the quantitative analysis of the insulin-producing ability of β-cells, immunostaining and H/E (Hematoxylin/Eosin) staining were conducted in the fixed pancreases, using antibodies, including an anti-insulin Ab, an anti-glucagon Ab, and anti-somatostatin Ab.

Figure 9:
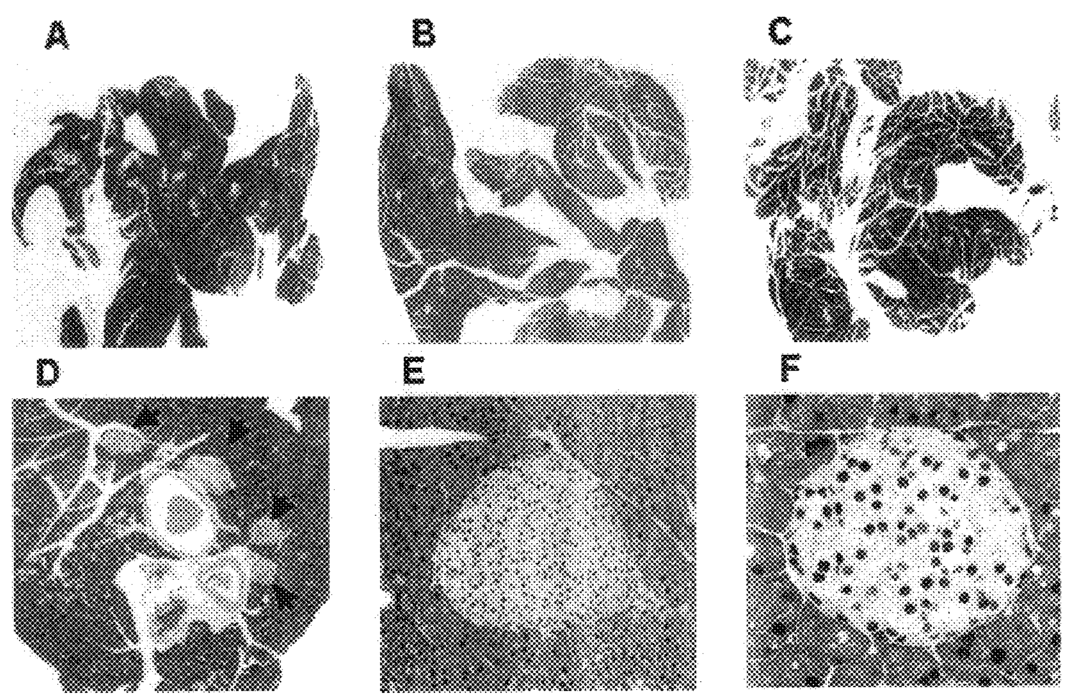
FIG. 9 shows microphotographs of murine pancreases, magnified by factors of 12.5 (upper panel: A, B, C) 40 (D), 200 (E) and 400 (F). In a normal pancreas (A), Langerhans islets are observed to be distributed around vessels. Normal Langerhans islets can be seen in more detail in photographs with higher magnifications (D, E, F). On the contrary, Langerhans islets are shrunken or disappear in the pancreas of a diabetic mouse (B). In the pancreas (C) of the mouse whose blood glucose level was reduced to a normal range by the injection of the insulin-expression vector (pUCK14-INS) after the induction of diabetic mellitus, Langerhans islets are observed to be destroyed.
Figure 10:
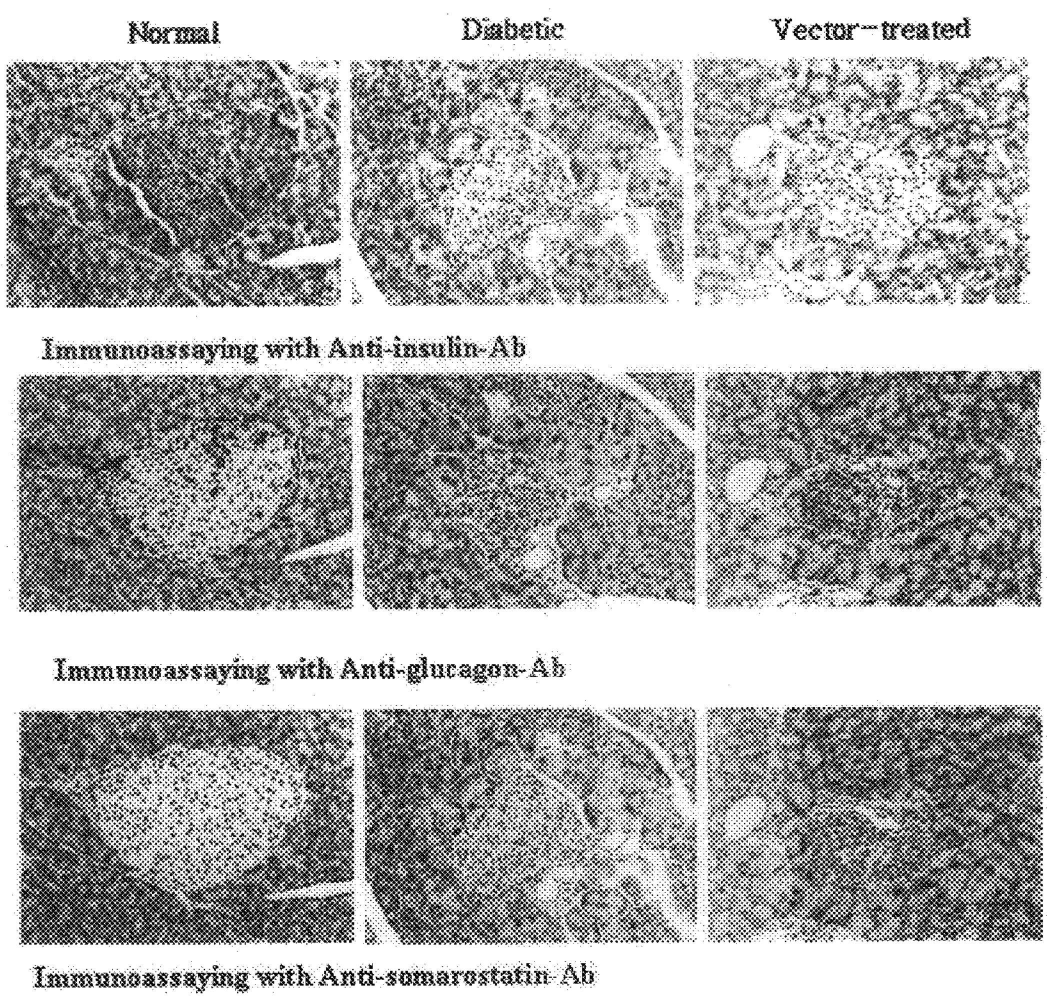
FIG. 10 shows microphotographs of Langerhans islets of non-treated normal mice (leftmost column), diabetic mice (middle column) and vector-injected normal mice (rightmost column), which were immunostained with an anti-insulin Ab (top panel), an anti-glucagon Ab (middle panel) and an anti-somatostatin Ab (bottom panel).

After the staining, photographs were taken of the pancreases. The results are given in FIG. 9. As seen in FIG. 9, an average of 10 Langerhans islets were distributed around veins in the normal pancreas whereas in diabetic mice, they had almost completely disappeared, or, if found, existed in very shrunken forms. As for the mice whose blood glucose levels were returned back to normal levels after the injection of the insulin expression vector, few or no Langerhans islets were found in their pancreases. In addition, their pancreases had collapsed morphologies. To examine which of the three kinds of pancreatic cells, α, β and δ cells, held islets, pancreases were immunoassayed with an anti-insulin Ab, an anti-glucagon Ab, and an anti-somatostatin Ab. Observation under a microscope, as shown in FIG. 10, showed that almost no β-cells existed and, instead, α-cells predominantly occupied the β-cell space in the pancreases of the diabetic mice with δ cells verging. Therefore, it can be concluded that, in the mice whose blood glucose levels were normalized by the injection of the insulin expression vector after the induction of diabetes mellitus with STZ, the keratinocytes in which the insulin gene were expressed from the vector injected were responsible for the maintenance of normal blood glucose levels, substituting the role which the pancreatic insulin-producing cells had played.

Taken together, the data obtained in above examples demonstrate that the helper vector containing a Drosophila's P-element sequence can help the insulin gene integrate effectively into the chromosome of keratinocytes. In addition, when being incorporated, along with the K14 promoter gent, to the chromosome, the insulin gene is found to be expressed strongly in vivo, thereby exerting its hormonal activity to maintain normal blood glucose levels. Furthermore, in contrast to conventional retrovirus delivery systems, the non-viral insulin vector of the present invention is safe and simple. In consequence, the present invention is very useful in treating insulin-dependent diabetes mellitus, making a great contribution to the gene therapy field.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A method for preparing an insulin expression vector, in which an insulin gene amplified from human genomic DNA by use of a pair of insulin primers represented by the following sequences (I) and a K14 promoter gene amplified by use of a pair of K14 primers represented by the following sequences (II) are inserted together into pUChsneo:

```
Insulin forward                                    (I)
5' CCTGCCTGTCTCCCAGAGCTCTGTCCTTCT3', SEQ ID NO. 3
Insulin reverse
5' GCAGGGCTGGTTCTAGAGCTTTATTCCATC3', SEQ ID NO. 4
```

-continued

```
K14 promoter Forward                              (II)
5' ATTGCTGAAGTTTTGATCTAGACACCTCCA3', SEQ ID NO. 5
K14 promoter Reverse
5' CTGAGTGAAGAGAAGGAGCTCGGGTAAATT3', SEQ ID NO. 6.
```

2. A non-viral insulin expression vector, pUCK14-INS constructed by the method of claim 1.

3. A base sequence encoding a K14 promoter and a human insulin gene of the insulin expression vector, pUCK14-INS represented by the sequence as shown in SEQ ID 7.

* * * * *

SEQUENCE LISTING

```
<160> NUMBER OF SEQ ID NOS: 7

<210> SEQ ID NO 1
<211> LENGTH: 21
<212> TYPE: DNA
<213> ORGANISM: Unknown
```

-continued

```
<220> FEATURE:
<223> OTHER INFORMATION: Primer sequence

<400> SEQUENCE: 1

tcactctaga aacagctatg a                                               21


<210> SEQ ID NO 2
<211> LENGTH: 18
<212> TYPE: DNA
<213> ORGANISM: Unknown
<220> FEATURE:
<223> OTHER INFORMATION: Primer sequence

<400> SEQUENCE: 2

tcgacccggt tattatta                                                   18


<210> SEQ ID NO 3
<211> LENGTH: 30
<212> TYPE: DNA
<213> ORGANISM: Homo sapiens

<400> SEQUENCE: 3

cctgcctgtc tcccagagct ctgtccttct                                      30


<210> SEQ ID NO 4
<211> LENGTH: 30
<212> TYPE: DNA
<213> ORGANISM: Homo sapiens

<400> SEQUENCE: 4

gcagggctgg ttctagagct ttattccatc                                      30


<210> SEQ ID NO 5
<211> LENGTH: 30
<212> TYPE: DNA
<213> ORGANISM: Unknown
<220> FEATURE:
<223> OTHER INFORMATION: Primer sequence

<400> SEQUENCE: 5

attgctgaag ttttgatcta gacacctcca                                      30


<210> SEQ ID NO 6
<211> LENGTH: 30
<212> TYPE: DNA
<213> ORGANISM: Unknown
<220> FEATURE:
<223> OTHER INFORMATION: Primer sequence

<400> SEQUENCE: 6

ctgagtgaag agaaggagct cgggtaaatt                                      30


<210> SEQ ID NO 7
<211> LENGTH: 2499
<212> TYPE: DNA
<213> ORGANISM: Unknown
<220> FEATURE:
<223> OTHER INFORMATION: base sequence encoding a K14 and a human
      insulin gene of the insulin expression vector pUC14-INS

<400> SEQUENCE: 7

attgctgaag ttttgatata cacacctcca aagcaggacc aagtggactc ctagaaatgt     60

cccctgaccc ttggggcttc aggagtcagg gaccctcgtg tccacctcag ccttgccctt    120

gcacagccca gctccactcc agcctctact cctccccaga acatctcctg ggccagttcc    180
```

-continued

```
acaaggggct caaacgaggg cacctgagct gcccacacta gggatgttct gggggtctga    240
gaagatatct ggggctggaa gaataaaagg ccccccctagg cctgttcctg gatgcagctc    300
cagccacttt ggggctaagc ctgggcaata acaatgccaa cgaggcttct tgccatactc    360
ggtttacaaa accctttaca tacattgtcg cattggattc tcagagctga ctgcactaag    420
cagaatagat ggtatgactc ccactttgca gatgagaaca ctgaggctca gagaagtgcg    480
aagccctggg tcacagaggc gtaaatgcag agccaggacc cacctgaaga cccacctgac    540
tccaggatgt ttcctgcctc catgaggcca cctgccctat ggtgtggtgg atgtgagatc    600
ctcaccatag ggaggagatt agggtctgtg ctcagggctg ggagaggtg cctggatttc    660
tctttgatgg ggatgttggg gtgggaatca cgatacacct gatcagctgg gtgtatttca    720
gggatggggc agacttctca gcacagcacg gcaggtcagg cctgggaggg ccccccagac    780
ctccttgtct ctaatagagg gtcatggtga gggaggcctg tctgtgccca aggtgacctt    840
gccatgccgg tgctttccag ccgggtatcc atcccctgca gcagcaggct tcctctacgt    900
ggatgttaaa ggcccattca gttcatggag agctagcagg aaactaggtt taaggtgcag    960
aggccctgct ctctgtcacc ctggctaagc ccagtgcgtg ggttcctgag ggctgggact   1020
cccagggtcc gatgggaaag tgtagcctgc aggcccacac ctccccctgt gaatcacgcc   1080
tggcgggaca agaaagccca aaacactcca aacaatgagt ttccagtaaa atatgacaga   1140
catgatgagg cggatgagag gagggacctg cctgggagtt ggcgctagcc tgtgggtgat   1200
gaaagccaag gggaatggaa agtgccagac ccgcccccta cccatgagta taaagcactc   1260
gcatcccttt gcaatttacc cgagctctgt ccttctgcca tggccctgtg gatgcgcctc   1320
ctgcccctgc tggcgctgct ggccctctgg ggacctgacc cagccgcagc ctttgtgaac   1380
caacacctgt gcggctcaca cctggtgaag ctctctacct agtgtgcggg gaacgaggct   1440
tcttctacac acccaagacc cgccgggagg cagaggacct gcagggtgag ccaaccgccc   1500
attgctgccc ctggccgccc ccagccaccc cctgctcctg gcgctcccac ccagcatggg   1560
cagaaggggg caggaggctg ccacccagca gggggtcagg tgaccttttt taaaaagaag   1620
ttctcttggt cacgtcctaa aagtgaccag ctccctgtgg cccagtcaga atctcagcct   1680
gaggacggtg ttggcttccg gcagccccga gatacattag agggtgggca cgctcctccc   1740
tccactcgcc cccctcaaac aaatgccccg cagcccattt ctccaccctc atttgatgac   1800
cgcagattca agtgttttgt taagtaaagt cctgggtgac ctggggtcac agggtgcccc   1860
acgctgcctg cctctgggcg aacaccccat cacgcccgga ggagggcgtg gctgcctgcc   1920
tgagtgggcc agacccctgt cgccaggcct cacggcagct ccatagtcag gagatgggga   1980
agatgctggg gacaggccct ggggagaagt actgggatca cctgttcagg ctcccactgt   2040
gacgctgccc cggggcgggg gaaggaggtg ggacatgtgg gcgttggggc ctgtaggtcc   2100
acacccagtg tgggtgaccc tccctctaac ctgggtccag cccggctgga gatgggtggg   2160
agtgcgacct agggctggcg ggcaggcggg cactgtgtct ccctgactgt gtcctcctgt   2220
gtccctctgc ctcgccgctg ttccggaacc tgctctgcgc ggcacgtcct ggcagtgggg   2280
caggtggagc tgggcggggg ccctggtgca ggcagcctgc agcccttggc cctggagggg   2340
tccctgcaga agcgtggcat tgtggaacaa tgctgtacca gcatctgctc cctgtaccag   2400
ctggagaact actgcaacta gacgcagcct gcaggcagcc ccacacccgc cgcctcctgc   2460
accgagagag atggaataaa gcccttgaac cagccctgc                          2499
```